US 8,163,236 B1

(12) United States Patent
Bacik et al.

(10) Patent No.: US 8,163,236 B1
(45) Date of Patent: Apr. 24, 2012

(54) TRANSPORTABLE DECONTAMINATION UNIT AND DECONTAMINATION PROCESS

(75) Inventors: Michael A. Bacik, Fairview, PA (US); Aaron L. Hill, Erie, PA (US); Peter J. Buczynski, Girard, PA (US); Richard A. Weiss, Willoughby, OH (US); Timothy W. Meilander, Broadview Heights, OH (US); Paul A. Wiget, Mentor, OH (US); Iain F. McVey, Lakewood, OH (US); Michael A. Centanni, Parma, OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 13/357,633

(22) Filed: Jan. 25, 2012

Related U.S. Application Data

(62) Division of application No. 12/033,904, filed on Feb. 20, 2008, now Pat. No. 8,128,888.

(60) Provisional application No. 60/893,134, filed on Mar. 6, 2007, provisional application No. 60/962,876, filed on Aug. 1, 2007.

(51) Int. Cl.
*A61L 2/00* (2006.01)
*A61L 9/00* (2006.01)
*B01J 19/00* (2006.01)

(52) U.S. Cl. .......... 422/28; 422/291; 422/292; 422/300; 422/29

(58) Field of Classification Search ............ 422/28, 422/29, 291, 292, 300
See application file for complete search history.

(56) References Cited

U.S. PATENT DOCUMENTS

| 2,348,574 | A | 5/1944 | Ross |
| 2,823,863 | A | 2/1958 | Moyes |
| 3,858,645 | A | 1/1975 | Egger |
| 3,994,684 | A | 11/1976 | Tomasulo |
| 4,675,923 | A | 6/1987 | Ashley |
| 4,743,430 | A | 5/1988 | Spielholz |
| 4,808,377 | A | 2/1989 | Childers et al. |
| 4,858,256 | A | 8/1989 | Shankman |
| 4,861,560 | A | 8/1989 | Nakajima |
| 4,909,988 | A | 3/1990 | Childers et al. |
| 4,993,199 | A | 2/1991 | Hughes |
| 5,114,670 | A | 5/1992 | Duffey |
| 5,258,162 | A | 11/1993 | Andersson et al. |
| 5,277,875 | A | 1/1994 | Albright et al. |
| 5,286,447 | A | 2/1994 | Fannin et al. |
| 5,405,587 | A | 4/1995 | Fernandez et al. |
| 5,472,004 | A | 12/1995 | Gilliard |
| 5,502,975 | A | 4/1996 | Brickley et al. |

(Continued)

FOREIGN PATENT DOCUMENTS

DE 195 06 200 2/1995
(Continued)

OTHER PUBLICATIONS

International Search Report and Written Opinion from corresponding Application No. PCT/US2008/054342 Mailed Jul. 3, 2008.

(Continued)

*Primary Examiner* — Kevin Joyner
(74) *Attorney, Agent, or Firm* — Renner, Otto, Boisselle & Sklar, LLP

(57) ABSTRACT

The disclosed invention relates to a portable decontamination unit. The invention also relates to a decontamination process. The decontamination unit may be ruggedized for use in hostile environments such as those that may be anticipated for military applications.

13 Claims, 6 Drawing Sheets

U.S. PATENT DOCUMENTS

| | | | |
|---|---|---|---|
| 5,520,893 A | 5/1996 | Kasting, Jr. et al. |
| 5,634,880 A | 6/1997 | Feldman et al. |
| 5,665,316 A | 9/1997 | Salonia et al. |
| 5,706,846 A | 1/1998 | Sutton |
| 5,868,667 A | 2/1999 | Lin et al. |
| 5,882,590 A | 3/1999 | Stewart et al. |
| 5,916,096 A | 6/1999 | Wiesmann et al. |
| 5,941,672 A | 8/1999 | Lapointe et al. |
| 5,958,336 A | 9/1999 | Duarte |
| 6,077,480 A | 6/2000 | Edwards et al. |
| 6,120,739 A | 9/2000 | Thomas et al. |
| 6,199,388 B1 | 3/2001 | Fischer, Jr. |
| 6,279,589 B1 | 8/2001 | Goodley |
| 6,488,902 B1 | 12/2002 | DeCato et al. |
| 6,517,639 B2 | 2/2003 | Toepfer et al. |
| 6,557,365 B2 | 5/2003 | Dinnage et al. |
| 6,645,450 B2 | 11/2003 | Stoltz et al. |
| 6,711,907 B2 | 3/2004 | Dinnage et al. |
| 6,734,405 B2 | 5/2004 | Centanni et al. |
| 6,751,964 B2 | 6/2004 | Fischer |
| 6,852,279 B2 | 2/2005 | Williams et al. |
| 6,867,393 B1 | 3/2005 | Lewis |
| 6,906,296 B2 | 6/2005 | Centanni et al. |
| 6,923,716 B2 | 8/2005 | Koeger |
| 6,928,143 B2 | 8/2005 | Menear et al. |
| 6,936,434 B2 | 8/2005 | McDonnell et al. |
| 6,953,549 B2 | 10/2005 | Hill et al. |
| 6,986,386 B2 | 1/2006 | Sekhar et al. |
| 7,047,751 B2 | 5/2006 | Dinnage et al. |
| 7,102,052 B2 | 9/2006 | McVey et al. |
| 7,144,550 B2 | 12/2006 | Devine et al. |
| 7,160,566 B2 | 1/2007 | Fink et al. |
| 7,203,979 B2 | 4/2007 | O'Brien |
| 7,308,798 B2 | 12/2007 | Caggiano |
| 2002/0015672 A1 | 2/2002 | Saint-Martin et al. |
| 2003/0129111 A1 | 7/2003 | Miller et al. |
| 2003/0138347 A1 | 7/2003 | Lin |
| 2003/0164091 A1 | 9/2003 | Hill et al. |
| 2004/0057868 A1 | 3/2004 | McVey et al. |
| 2004/0184950 A1 | 9/2004 | McVey et al. |
| 2004/0197252 A1 | 10/2004 | Parrish |
| 2005/0005533 A1 | 1/2005 | Stewart et al. |
| 2005/0175500 A1 | 8/2005 | Adams et al. |
| 2005/0214159 A1 | 9/2005 | Schwei et al. |
| 2005/0217710 A1 | 10/2005 | Kaipaninen |
| 2005/0220666 A1 | 10/2005 | Foster |
| 2006/0008379 A1 | 1/2006 | Mielnik et al. |
| 2006/0018788 A1 | 1/2006 | Monico et al. |
| 2006/0099121 A1 | 5/2006 | Doona et al. |
| 2006/0252974 A1 | 11/2006 | McVey et al. |
| 2006/0270887 A1 | 11/2006 | Watkins |
| 2007/0098592 A1 | 5/2007 | Buczynski et al. |
| 2007/0274858 A1 | 11/2007 | Childers et al. |
| 2008/0279722 A1 | 11/2008 | Bacik et al. |

FOREIGN PATENT DOCUMENTS

| | | |
|---|---|---|
| EP | 1 393 751 | 3/2004 |
| WO | 2005/035067 | 4/2004 |
| WO | 2004/110504 | 12/2004 |
| WO | 2007/102798 | 9/2007 |

OTHER PUBLICATIONS

Co-pending U.S. Appl. No. 12/033,904, filed Feb. 20, 2008.

TRANSPORTABLE DECONTAMINATION UNIT AND DECONTAMINATION PROCESS

This application is a divisional of U.S. patent application Ser. No. 12/033,904 filed on Feb. 20, 2008, now U.S. Pat. No. 8,128,888 which claims the benefit under 35 U.S.C. §119(e) to of U.S. Provisional Application No. 60/893,134 filed on Mar. 6, 2007 and U.S. Provisional Application No. 60/962,876 filed on Aug. 1, 2007. These applications are incorporated herein by reference in their entireties.

TECHNICAL FIELD

This invention relates to a transportable decontamination unit and to a decontamination process.

BACKGROUND

Decontaminant generating systems, such as those used to generate vaporous hydrogen peroxide (VHP), have been used to decontaminate large enclosures such as rooms and buildings (e.g., hotel rooms, hospital wards, scientific laboratories, etc.) from contaminants such as bacteria, molds, fungi, yeasts, and the like.

SUMMARY

It would be advantageous for the military to use these decontaminant systems in the field in defense against chemical and biological weapons. However, a problem with these decontamination systems is that they are not readily transportable. This invention provides a solution to this problem. This invention relates to a decontamination unit that is self-contained, readily transportable and has a relatively large-scale decontamination chamber. This invention relates to a transportable decontamination unit, comprising: a housing containing a decontamination chamber and a decontaminant processing section; the decontamination chamber comprising a first entrance with a first door, the first entrance being adapted for placing articles to be decontaminated in the decontamination chamber, and an opposite second entrance with a second door, the second entrance being adapted for removing decontaminated articles from the decontamination chamber, the decontamination chamber including at least one gas inlet for admitting a decontaminant air stream into the decontamination chamber and at least one gas outlet for permitting a gaseous air stream to flow out of the decontamination chamber; the decontaminant processing section comprising a power generator and a decontaminant generator, the power generator being adapted for providing power for the decontaminant generator, the decontaminant generator being adapted for destroying residual amounts of decontaminant in the gaseous air stream, dehumidifying the gaseous air stream, and adding decontaminant to the gaseous air stream to form the decontaminant air stream.

This invention relates to a process for operating the foregoing decontamination unit, comprising: opening the first door; placing one or more contaminated articles in the decontamination chamber; closing the first door; operating the power generator to provide power to operate the decontaminant generator; flowing the decontaminant air stream from the decontaminant processing section into the decontamination chamber; contacting the contaminated articles in the decontamination chamber with the decontaminant air stream to decontaminate the contaminated articles; flowing the gaseous air stream from the decontamination chamber back to decontaminant processing section; opening the second door; and removing the decontaminated articles from the decontamination chamber.

BRIEF DESCRIPTION OF THE DRAWINGS

In the annexed drawings all parts and features have like references. A number of the annexed drawings are schematic illustrations which are not necessarily proportioned accurately or drawn to scale.

DETAILED DESCRIPTION

Figure 1:
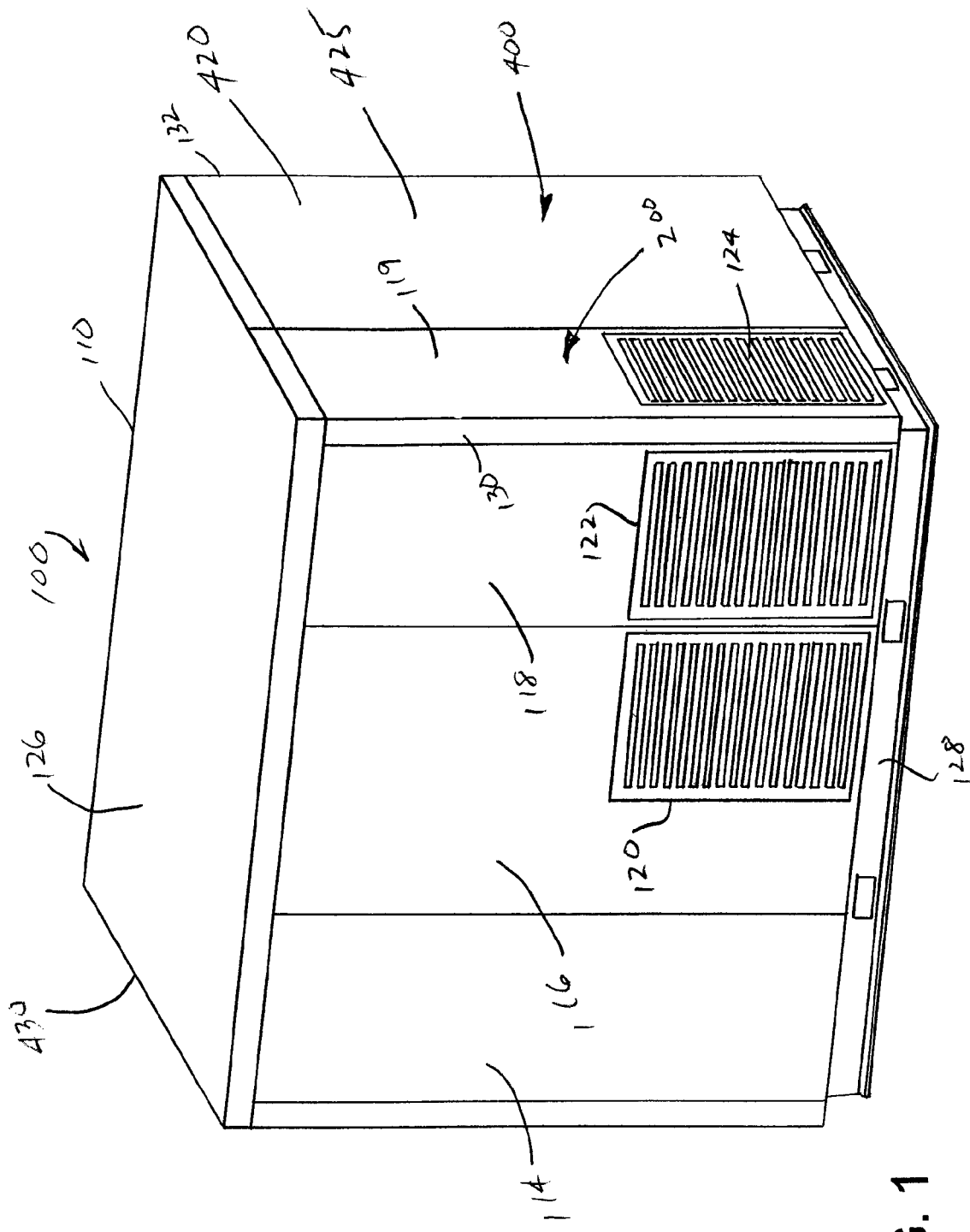
FIG. 1 is a schematic illustration of a decontamination unit within the scope of the present invention. The decontamination unit includes a decontaminant processing section and a decontamination chamber.

All ranges and ratio limits disclosed in the specification and claims may be combined in any manner. It is to be understood that unless specifically stated otherwise, references to "a", "an", and/or "the" may include one or more than one, and that reference to an item in the singular may also include the item in the plural. All combinations specified in the claims may be combined in any manner.

The term "ruggedized," and like terms such as "ruggedization," are used herein to refer to apparatus that is: (1) hardened to ensure that five exposures to chemical, biological, radiological or nuclear (CBRN) contaminants, decontaminants and decontaminating procedures over a thirty-day period do not cause the apparatus to require corrective maintenance during that thirty-day period; (2) capable of being used at temperatures ranging from about −32° C. to about 49° C.; (3) capable of being used in relative humidities ranging from about 5% to about 100%; and/or (4) capable of operating when exposed to conventional hazards of solar radiation, rain, fungus, salt fog, sand, dust, vibration and/or shock in accordance with Military Standard 810 (MIL-STD-810).

The term "line" when referring to the drawings may refer to any conduit for conveying a fluid. The conduit may be in any desired form, for example, one or more pipes, tubings, channels, and the like. These may be made of materials sufficient to provide the required properties of strength, flexibility, and resistance to the fluids being conveyed. The lines may be ruggedized to permit use in hostile environments such as those that may be encountered in military applications.

The term "fluid" may refer to a liquid, gas, or mixture thereof.

The inventive decontamination unit, in its illustrated embodiment, will be described with reference to FIGS. 1-6. Referring to FIGS. 1-6, decontamination unit 100 comprises housing 110 which contains decontaminant processing section 200 and decontamination chamber 400. The housing 110 includes removable side panels 114, 116 and 118, side panel 119, and vents 120, 122 and 124. The housing 110 includes top panel 126. The decontamination unit 100 is positioned on pallet 128. Part of the housing 110 forms the exterior walls of the decontamination chamber 400.

The decontamination unit 100 may be of sufficient size and weight to provide the decontamination chamber 400 with the desired internal volume to provide for decontamination on a large scale and yet allow the decontamination unit 100 to be readily transportable. The decontamination chamber 400 may have an internal volume in the range from about 0.5 to about 10 cubic meters, and in one embodiment from about 2.5 to about 7.5 cubic meters, and in one embodiment from about 4 to about 7 cubic meters, and in one embodiment from about 6 to about 7 cubic meters, and in one embodiment about 6.8 cubic meters. The decontamination unit 100 may have a height (as measured from the base support 128 to the top panel 126) in the range from about 0.5 to about 2.5 meters, and in one embodiment in the range from about 1 to about 2.5 meters, and in one embodiment in the range from about 1.5 to about 2.5 meters, and in one embodiment in the range from about 2 to about 2.5 meters, and in one embodiment in the range from about 2.3 to about 2.5 meters, and in one embodiment about 2.4 meters. The decontamination unit 100 may have a width (as measured from side 130 to side 132) in the range from about 1 to about 2.5 meters, and in one embodiment in the range from about 1.5 to about 2.5 meters, and in one embodiment in the range from about 2 to about 2.5 meters, and in one embodiment about 2.2 meters. The decontamination unit 100 may have a length (as measured from the first entrance 420 to the second entrance 430) in the range from about 1.2 to about 2.8 meters, and in one embodiment in the range from about 2 to about 2.8 meters, and in one embodiment in the range from about 2.5 to about 2.8 meters, and in one embodiment about 2.7 meters. The overall weight of the decontamination unit 100 may be in the range from about 500 to about 10,000 pounds (227 to 4536 Kg), and in one embodiment in the range from about 500 to about 7,500 pounds (227 to 3402 Kg), and in one embodiment in the range from about 1000 to about 7500 pounds (454 to 3402 Kg), and in one embodiment about 5000 pounds (2268 Kg). The decontamination unit 100 may be readily transported using conventional techniques, for example, the decontamination unit 100 may be transported using an airplane, ship, truck, and the like. The decontamination unit is positioned on and may be transported using pallet 128. Pallet 128 may be a standard military 463L master pallet.

The 463L master pallet is used for air transport by the United States Air Force. Cargo aircraft used by the United States Air Force may be configured to accept these pallets. The 463L master pallet is also used for combat offloads and aerial delivery or airdrop. The 463L master pallet is 88 inches (224 cm) wide, 108 inches (274 cm) long, and 2.25 inches (5.7 cm) high. The usable space is 84 inches (213 cm) by 104 inches (264 cm). The 463L master pallet may hold up to 10,000 pounds (4500 Kg) of cargo. The empty weight is 290 pounds (130 Kg). The 463L master pallet has a balsa wood core which is surrounded by a thin aluminum skin. There are 22 rings surrounding the edge, each rated at 7,500 pounds (3400 Kg).

The decontamination unit 100 may be used in hostile environments such as those that may be anticipated for military applications. When intended for use in such hostile environments the housing 110 as well as the decontamination chamber 400 may be ruggedized. Ruggedization may include resistance to anticipated operating conditions and hazards, including hot and cold temperatures, exposure to solar radiation, rain, fungus, salt fog, sand, dust, vibration and/or shock, as well as exposure to CBRN contaminants. The decontamination chamber 400 may be constructed of materials capable of withstanding exposure to decontaminants that may be used in the decontamination chamber 400 as well as the contaminants likely to be encountered. The decontamination chamber 400 may be insulated. The housing 110 and the decontamination chamber 400 may be constructed using any material that is sufficient to provide the apparatus with the desired properties of strength and yet be sufficiently lightweight to be transportable as well as being ruggedized. The materials of construction may include stainless steel, coated steel, aluminum, aluminum alloy, anodized aluminum, and the like. Various metal alloys may be used, including the stainless steel alloys SS304 and SS316, and aluminum alloy 6061. Non-reactive materials, such as polytheylene, polyvinyl chloride, fluorinated polymers such as polytetrafluoroethylene, and the like, may be used.

The decontaminant processing section 200 may include power generator 205 and decontaminant generator 260. The power generator 205 may include internal combustion engine 210 and electric generator 250. Alternatively, the power generator may comprise a fuel cell. The decontamination unit 100 may be regarded as being self-contained due to the fact that all of the power required to operate the decontaminant generator 260 may be provided by the power generator.

Figure 2:
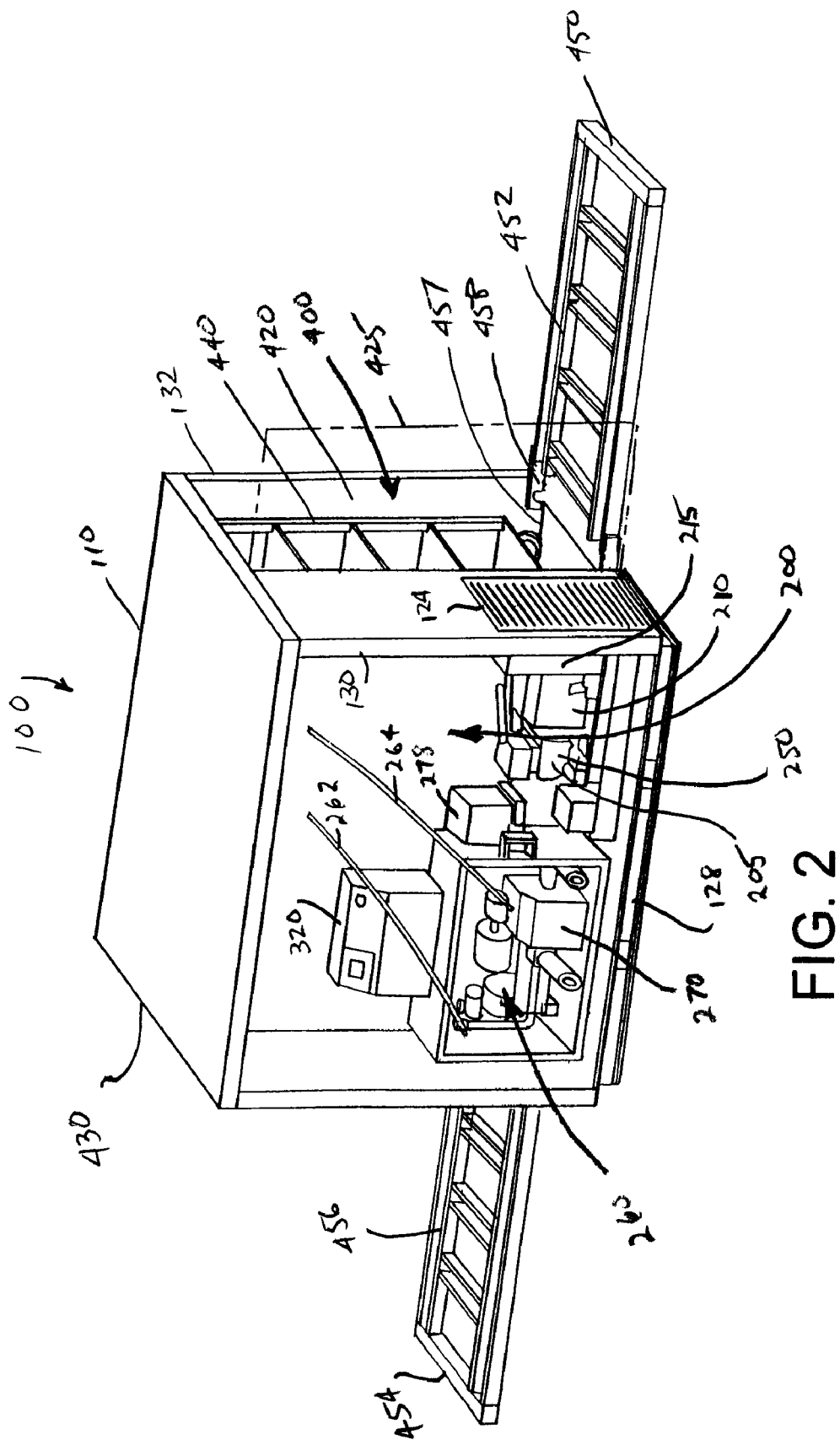
FIG. 2 is a schematic illustration of the decontamination unit illustrated in FIG. 1 with sides of the unit removed to show the interior of the decontaminant processing section. The decontaminant processing section includes a power generator, decontaminant generator, and control unit. Part of the interior of the decontamination chamber as well as a loading cart for use in the decontamination chamber are also shown. Portable tracks for rolling the loading cart into one side of the decontamination chamber and removing the loading cart from the other side of the decontamination chamber are shown.
Figure 3:
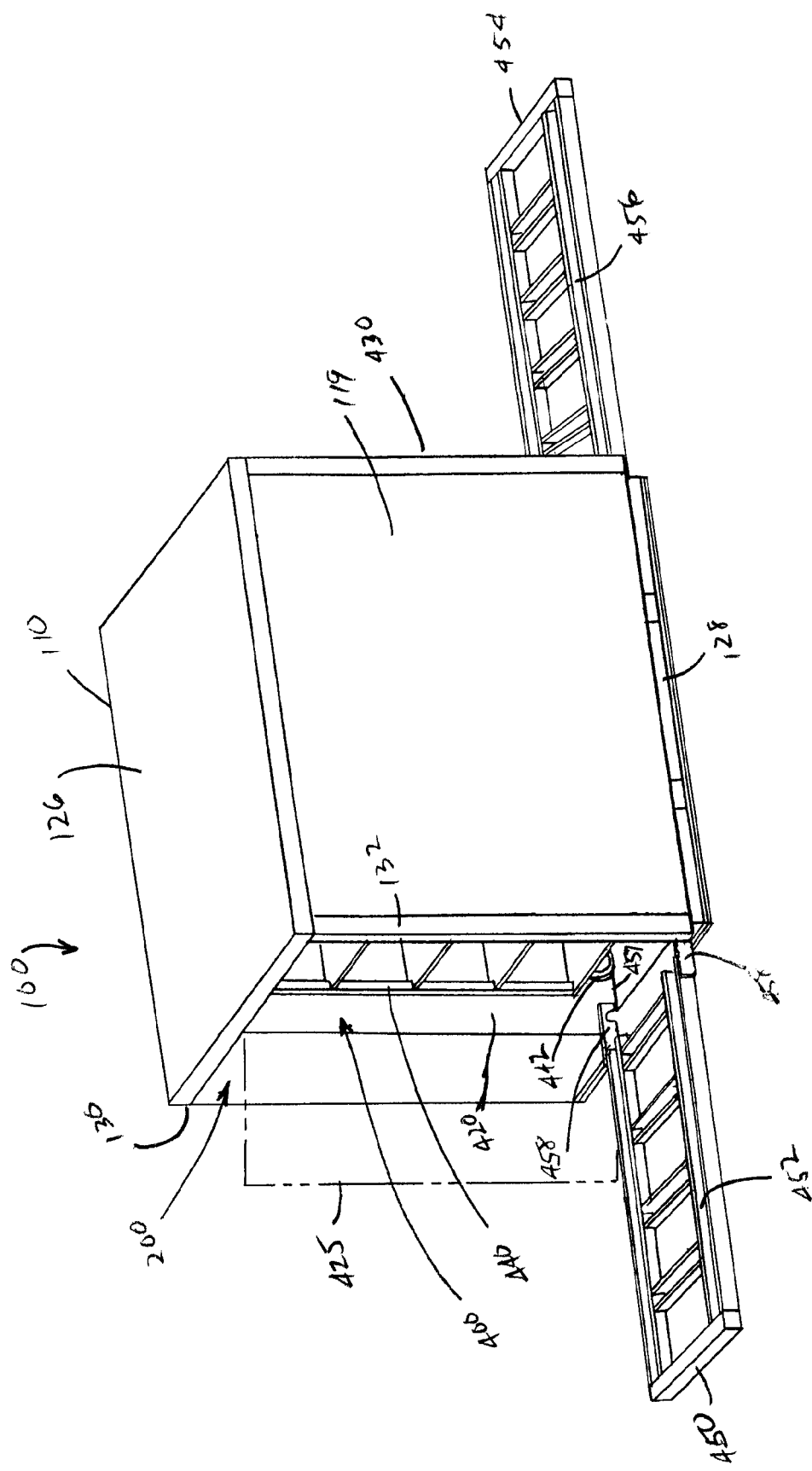
FIG. 3 is a view of the decontamination unit illustrated in FIG. 2 taken from the opposite side shown in FIG. 2.
Figure 4:
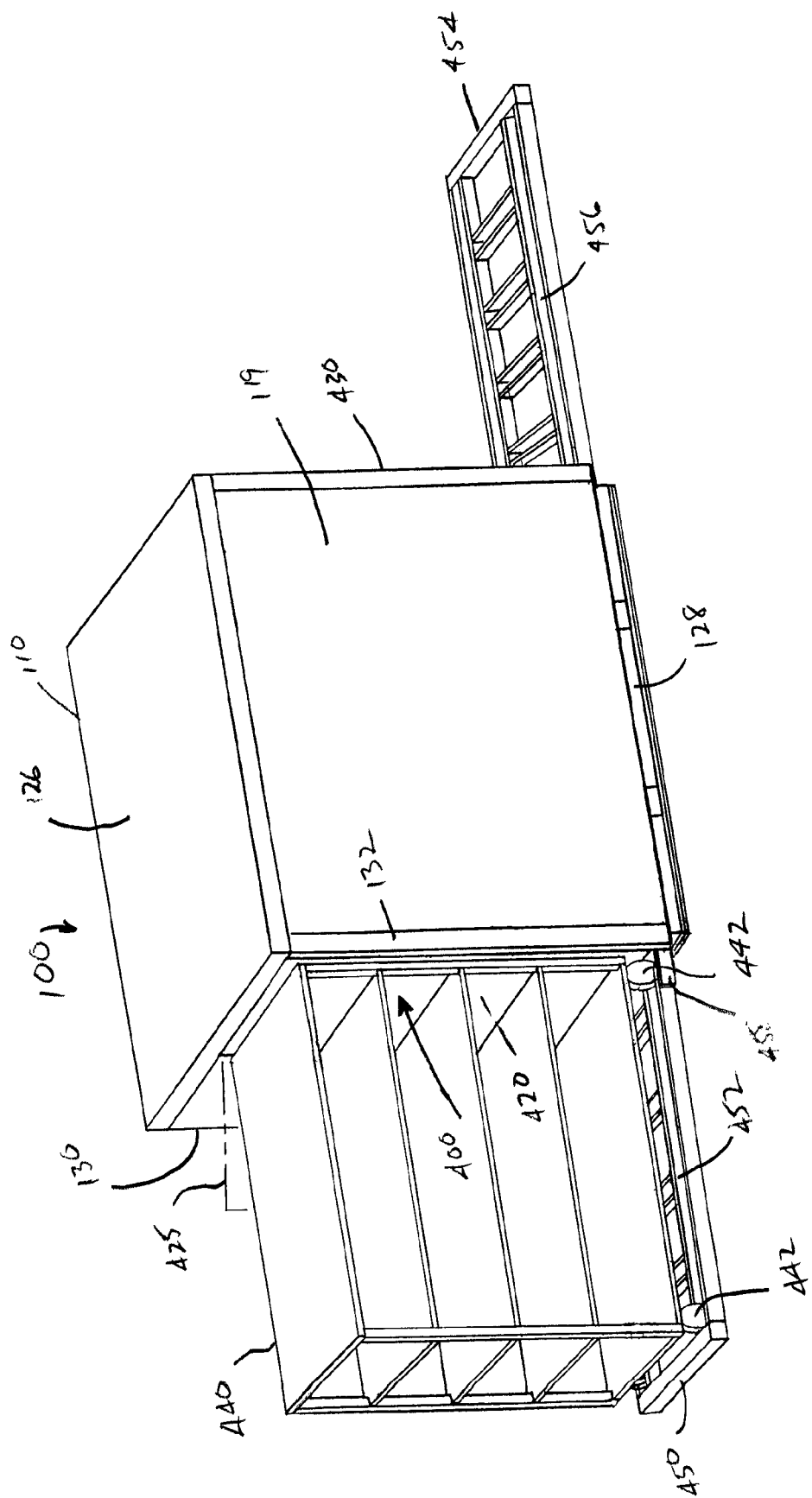
FIG. 4 is a view of the decontamination unit illustrated in FIG. 3 with the loading cart removed from the decontamination chamber and positioned on one of the portable tracks located outside the decontamination chamber.
Figure 5:
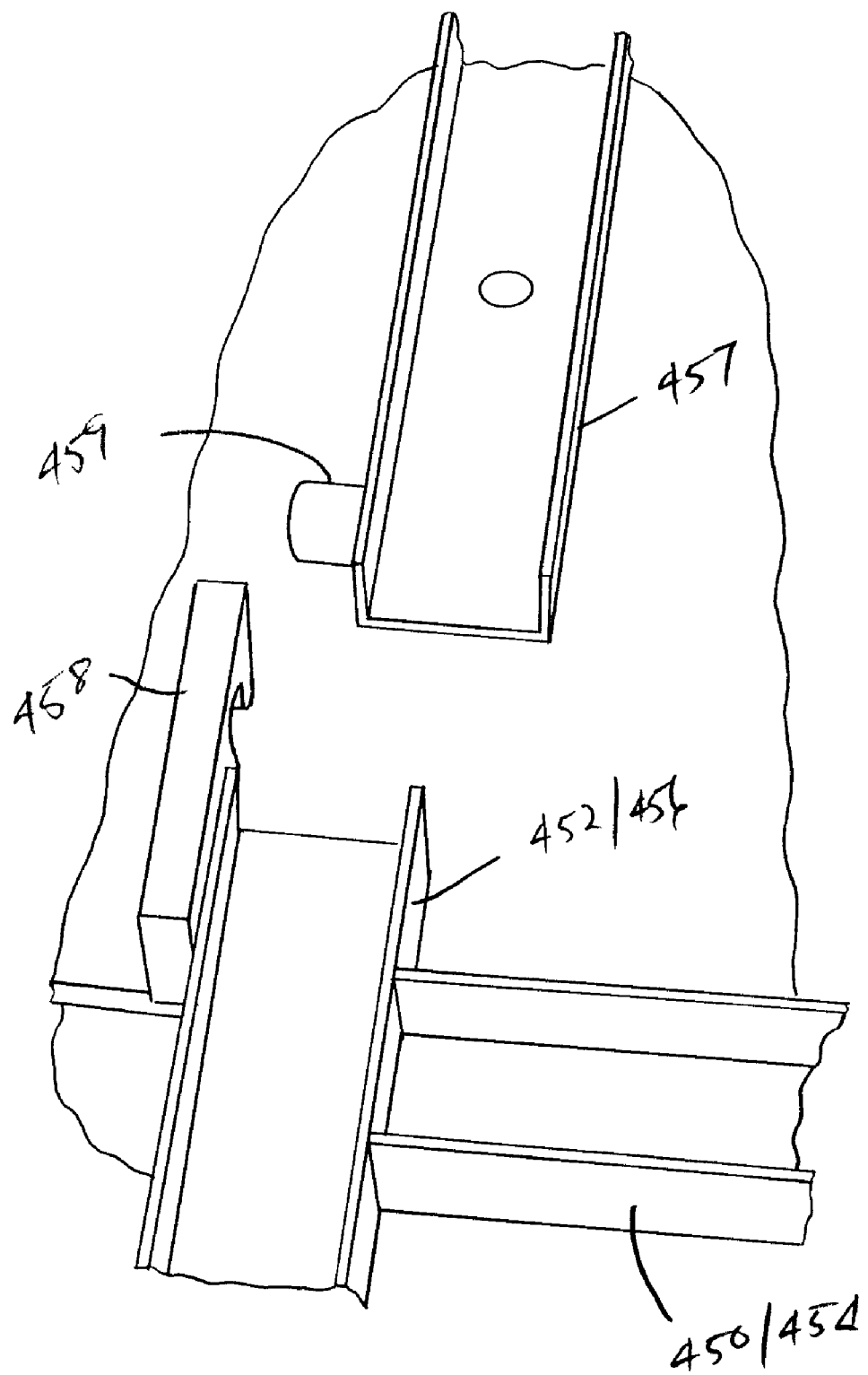
FIG. 5 is a schematic illustration showing a locking mechanism for connecting the portable tracks illustrated in FIGS. 2-4 to interior tracks in the decontamination chamber.
Figure 6:
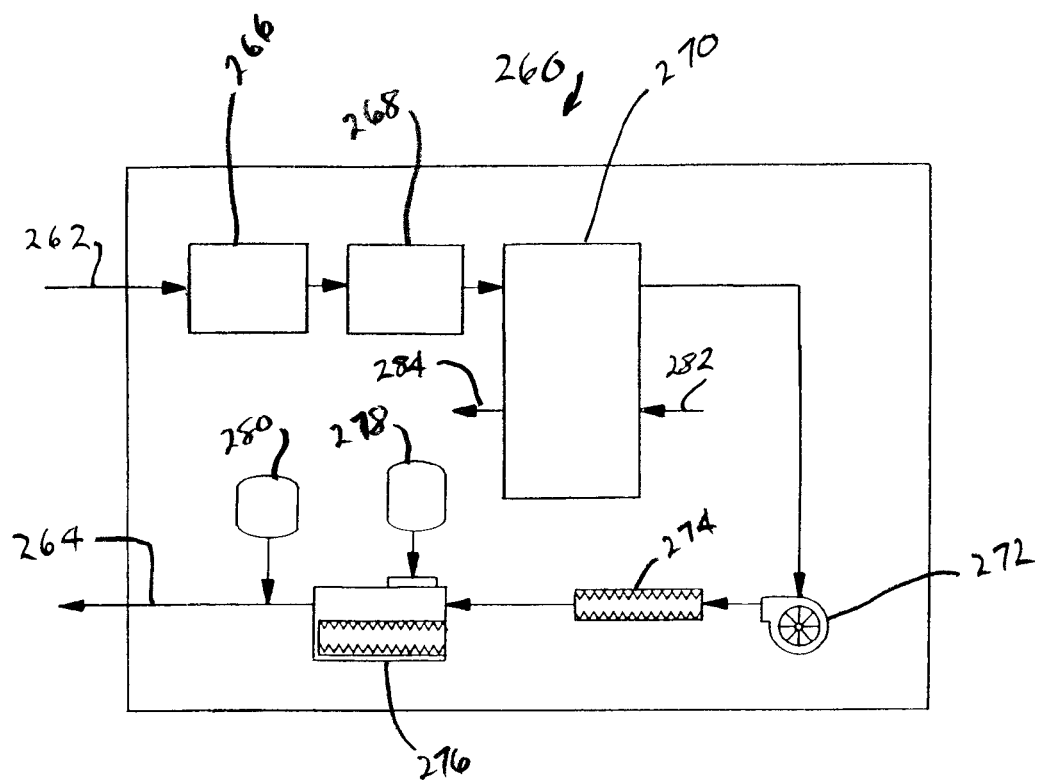
FIG. 6 is a flow sheet showing the operation of the decontaminant generator illustrated in FIG. 2.

The power generator 205 may comprise internal combustion engine 210 in combination with electric generator 250 as shown in FIG. 2. The internal combustion engine 210 may comprise any internal combustion engine that is suitable for providing sufficient power to operate the electric generator 250. The internal combustion engine 210 may be operated using diesel fuel, gasoline, petroleum gas, propane gas, natural gas, liquefied petroleum gas, hydrogen gas, biofuels (e.g., ethanol, biodiesel fuel, etc.), and the like. The internal combustion engine 210 may comprise a spark ignition engine or a compression ignition engine. The internal combustion engine 210 may comprise a two-cycle engine, four-cycle engine, rotary engine, or gas turbine engine.

The electric generator 250 may comprise any electric generator that can be powered by the internal combustion engine 210 and provide sufficient power to operate the decontaminant generator 260, as well as any other electrically powered equipment used with the decontamination unit 100 including lighting, electrically operated blowers, computers, monitors, controllers, recorders, and the like. The electric generator 250 may have a power rating in the range from about 4 to about 30 kVA, and in one embodiment in the range from about 4 to about 20 kVA, and in one embodiment in the range from about 4 to about 10 kVA.

The power generator 205 may comprise the internal combustion engine 210 and the electric generator 250 combined as a single piece of equipment. The power generator 205 may be ruggedized to permit use in hostile environments such as those that may be anticipated for military applications. The power generator may be sufficiently small and lightweight to allow the decontamination unit 100 to be transportable.

An example of a power generator that may be used is available from Northern Lights under the trade designation NL673L2. This power generator employs a Lugger L844 engine which is a vertical, three cylinder diesel engine. The Lugger L844 engine is a four cycle, liquid cooled, naturally aspirated, overhead valve, industrial-duty, diesel engine. This engine may operate at 1500 RPM or 1800 RPM. The AC output of the electric generator may be 6 kW or 5 kW. The specifications and dimensions for this power generator may be as follows:

| AC Output | |
|---|---|
| 6 kW | 60 Hz, 1800 RPM, 1 Ph, 1.0 PF, 120-240 V/25 A, 120 V/50 A |
| 5 kW | 50 Hz, 1500 RPM, 1 Ph, 1.0 PF, 220 V/22.7 A |
| Engine | |
| Displacement | 46.4 in$^3$ (0.76 ltr) |
| Bore/Stroke | 2.64/2.83 in (67/72 mm) |
| HP @ RPM | 9.9/1800 7.7/1500 |
| Approx. Fuel Use | |
| 1800 RPM @ full load | 0.59 gph (2.2 lph) |
| 1800 RPM @ full load | 0.32 gph (1.2 lph) |
| 1500 RPM @ full load | 0.50 gph (1.9 lph) |
| 1500 RPM @ full load | 0.28 gph (1.1 lph) |

The NL 673L2 power generator may have a base length of 32.8 inches (83.4 cm), a base width of 15.3 inches (39.40 cm), a height of 27 inches (68.6 cm), and a dry weight of 377 pounds (171 kg). Additional information concerning this power generator may be found at http://www.northern-lights.com/PDFs/brochurepdfs/NL673L2.pdf.

As an alternative to the internal combustion engine 210 and electric generator 250, the power generator may comprise a fuel cell. The fuel cell may be regarded as an electrochemical energy conversion device. It produces electricity from various external quantities of fuel (on an anode side) and oxidant (on a cathode side). These react in the presence of an electrolyte. Generally, the reactants flow in and reaction products flow out while the electrolyte remains in the cell. Various combinations of fuel and oxidant may be used. The fuel call may comprise a hydrogen cell which uses hydrogen as the fuel and oxygen as the oxidant. Other fuels may include hydrocarbons and alcohols. Other oxidants may include air, chlorine and chlorine dioxide. The fuel cell may work by catalysis, separating the component electrons and protons of the reactant fuel, and forcing the electrons to travel through a circuit, hence converting them to electrical power. The catalyst may comprise a platinum group metal or alloy. Another catalytic process takes the electrons back in, combining them with the protons and the oxidant to form waste products (typically water and carbon dioxide).

The decontaminant generator 260 may include gas inlet line 262, gas outlet line 264, catalytic converter 266, filter 268, desiccant wheel 270, blower 272, heater 274, vaporizer 276, liquid decontaminant container 278, and alkaline gas container 280. The power to operate the various components of the decontaminant generator 260 may be provided by the power generator 205.

In the operation of the decontaminant generator 260, a gaseous air stream comprising spent gases flows from the decontamination chamber 400 through line 262 into and through catalytic converter 266, and from the catalytic converter 266 through filter 268 to desiccant wheel 270, and then from desiccant wheel 270 to blower 272. The catalytic converter 266 may be used to destroy residual amounts of the decontaminant that may be in the gaseous air stream. For example, the catalytic converter 266 may be use to convert residual hydrogen peroxide to water vapor and oxygen. The catalyst may comprise any transition metal, transition metal oxide, or combination thereof, having the desired catalytic properties. The catalyst may comprise Ag, Mn, Pd, Pt, Rh, an oxide of one or more of the foregoing metals, or a mixture of two or more of the foregoing metals and/or oxides. The catalyst may be supported by a suitable support such as an alumina support. The catalyst may comprise silver in the form of a screen or screen plating. The catalyst may comprise a silver based alloy. The catalyst may comprise manganese dioxide. The catalyst may be in the form of a bed of particulate solids. The filter 268 may comprise a carbon filter and a high efficiency particle air (HEPA) filter. The desiccant wheel 270 may contain a desiccant material such as lithium chloride, silica gel, molecular sieves, and the like. The desiccant material may be used to absorb moisture from the gaseous air stream and thereby dehumidify the gaseous air stream. A regenerative air stream may flow through the desiccant wheel 270 as indicated by arrows 282 and 284. The gaseous air stream may flow from the desiccant wheel 270 through blower 272 to heater 274 where it may be heated. The gaseous air stream may flow from the heater 274 into vaporizer 276. Liquid decontaminant may flow from liquid decontaminant container 278 into the vaporizer 276. The liquid decontaminant may be vaporized in vaporizer 276 and combined with the gaseous air stream to form the decontaminant air stream. The decontaminant air may flow out of the vaporizer 276 through line 264. Optionally, an alkaline gas such as ammonia may flow from alkaline gas container 280, which may be a pressurized cartridge, to line 264 where it may be combined with the decontaminant air stream.

The decontaminant may comprise one or more oxidants such as peracids (e.g., peracetic acid) and/or peroxides (e.g., hydrogen peroxide), and the like. Oxidants such as hypochlorites, ozone, and the like, may be used. Mixtures of two or more of these may be used. Aqueous solutions of these oxidants may be used. The decontaminant may be combined with a solvent. The solvent may be miscible with water. When the decontaminant comprises hydrogen peroxide, the solvent may be used to enhance the solubility of the hydrogen peroxide and its associated decomposition products in the contaminant and thereby enhance the rate of destruction of the contaminant. The solvent may comprise a mixture of water and tert-butyl alcohol; water and acetonitrile; or water, acetonitrile and isopropyl alcohol. Other suitable solvents may include tetrahydrofuran, dimethylsulfoxide, acetone, acetaldehyde, propylene oxide, acetamide, diethylamine, dimethoxyethane, or a mixture of two or more thereof. The solvent concentration in the combined mixture of decontaminant and solvent may be in the range up to about 60% by weight solvent, and in one embodiment in the range from about 20 to about 60% by weight solvent. The decontaminant may be combined with an alkaline gas such as ammonia in applications wherein an increase in the pH of the decontaminant may be desired.

Vaporous hydrogen peroxide (VHP), which may be generated from an aqueous solution of hydrogen peroxide, may be used as the decontaminant. The aqueous solution may comprise from about 30% to about 40% by weight hydrogen peroxide, and in one embodiment about 35% by weight hydrogen peroxide; and from about 60% to about 70% by weight water, and in one embodiment about 65% by weight water. By adding an alkaline gas that is soluble in the hydrogen peroxide (ammonia, for example), the pH of the decontaminant may be controlled. The volumetric ratio of VHP to ammonia gas may be in the range from about 1:1 to about 1:0.0001.

VHP, when used in combination with ammonia gas, may be referred to as modified VHP or mVHP. VHP and/or mVHP may be effective microbial and chemical decontaminants because they may provide a broad spectrum of activity against a wide variety of pathogenic microorganisms and chemical pathogenic agents, such as hard to destroy spores of *Bacillus stearothermophilus, Bacillus anthracis*, smallpox virus, and the like. They may be also effective at or close to room temperature (e.g., about 15 to about 30° C.), making them suitable for use in the decontamination chamber 400 with little or no heating. VHP and/or mVHP may have good material compatibility, rendering them safe for use with a variety of equipment and materials, including electronic equipment, soft furnishings, brass and chrome fixtures, and the like. VHP may degrade to water and oxygen over time, which may not be harmful to a person subsequently entering the decontamination chamber 400. Low levels of hydrogen peroxide (for example, about 1 ppm, or less) that may remain in the decontamination chamber 400 after the decontamination process has been completed may not be considered to pose a risk to a person entering the chamber.

The decontamination chamber 400 may be referred to as a double-door decontamination chamber. The decontamination chamber 400 may have a first entrance 420 with a first door 425, and an opposite second entrance 430 with a second door (not shown). The first entrance 420 may be referred to as the "contaminated" side of the decontamination chamber and the second entrance 430 may be referred to as the "clean" side of the decontamination chamber. A loading cart 440 may be used to load contaminated articles into the decontamination chamber and unload decontaminated articles from the decontamination chamber 400. The decontamination chamber 400 may be operated by placing the contaminated articles on the loading cart 440. The first door 425 on the contaminated side 420 of the decontamination chamber 400 may be opened and the cart may be rolled into the decontamination chamber 400. The first door 425 may then be closed.

The decontaminant air stream may flow from the decontaminant processing section 200 into the decontamination chamber 400. The decontaminant air stream may circulate in the interior of the decontamination chamber 400, contact contaminated articles positioned in the decontamination chamber 400, and decontaminate the contaminated articles. A gaseous air stream comprising spent gases (i.e., air, residual decontaminant, residual hazardous biological and/or chemical materials, etc.) may flow from the decontamination chamber 400 back to the decontaminant air processing section 200. The decontamination process may be controlled using control unit 320. The decontamination chamber 400 may include one or more internal blowers for circulating gas in the decontamination chamber 400. The blowers may be powered by the power generator 205. The decontamination chamber 400 may contain internal monitors for measuring decontaminant levels, temperature, internal gas flow, and the like. These monitors may be used in combination with controllers for adjusting decontaminant concentration levels, temperature, internal gas flow rates, and the like.

When the decontaminant air stream flows into the decontamination chamber 400 and contacts the contaminated articles to be decontaminated, the process may be regarded as a dry process characterized by the absence of condensate formation on the surfaces of the contaminated articles being decontaminated. Alternatively, the process may be regarded as a wet process characterized by the formation of a condensate in the form of a liquid film on the surfaces of the contaminated articles. The liquid film may have a film layer thickness in the range up to about 20 microns, and in one embodiment up to about 10 microns, and in one embodiment up to about 5 microns, and in one embodiment up to about 1 micron. The film layer may be referred to as a microcondensate layer of hydrogen peroxide.

The progress of the decontamination process may be monitored using one or more decontamination or sterilization indicators. These indicators may contain a biological indicator. The biological indicator may comprise one or more test organisms which may be more resistant to the decontamination process than the organisms to be destroyed by the decontamination process. The test organism may be placed in contact with an incubation medium to determine whether the decontamination process was effective.

Upon completion of the decontamination process, the second door on the clean side 430 of the decontamination chamber may be opened and the loading cart 440 may be rolled out and unloaded.

The loading cart 440 may have any desired shape and design so long as it is suitable for traveling into and out of the decontamination chamber 400, and being held in the decontamination chamber 400 during operation of the decontamination process and/or transport of the decontamination unit 100. The loading cart 440, as depicted in the drawings, includes a number of solid shelves, and open sides. Alternatively, each of the shelves may be perforated or grated. The perforated or grated shelves may be advantageous for permitting internal circulation of the decontaminant air stream within the decontamination chamber 400. The loading cart 440 may have sidewalls which may be solid or they may be perforated or grated. The loading cart 440 may not have any shelves, and it may optionally have sidewalls that may be solid or may be perforated or grated.

The loading cart 440 may be positioned on platform frame 450, which may be located in front of the contaminated side 420 of the decontamination chamber 400, while the loading cart is loaded with contaminated articles. The platform frame 450 includes tracks 452 which are adapted for supporting the wheels 442 of the cart 440. The loading cart 440 may be pushed into the decontamination chamber 400 after which the door 425 may be closed and the decontamination process commenced. The decontamination chamber 400 includes interior tracks 457 which are provided to permit a facilitated and stabilized movement of the loading cart 440 into and out of the decontamination chamber 400. Upon completion of the decontamination process, the door on the clean side of the decontamination chamber 400 may be opened and the loading cart 440 may be rolled out of the decontamination chamber 400 on platform frame 454. The platform frame 454 includes tracks 456 for supporting the cart wheels 442. The platform frames 450 and 454 may include notched brackets 458 which are adapted to engage knobs 459 which are mounted on sides of the interior tracks 457. The resulting locking mechanisms allow the portable platform frames 450 and 454 to be releasably attached to the contaminated and clean sides of the decontamination chamber 400. This provides for the portable tracks 452 and 456 to be properly aligned with the interior tracks 457. It will be understood by those skilled in the art that a single platform frame may be used rather than the two platform frames 450 and 454 discussed above. The single platform frame may be used on the contaminated side during loading, and then on the clean side during unloading. The loading cart 440 and the platform frames 450 and 454 may be stored in the decontamination chamber 400 while the decontamination unit 100 is being transported. Alternatively, the platform frames 450 and 454 may be mounted on top or on the side of the decontamination unit 100 during transport of the decontamination unit.

The temperature of the decontaminant air stream entering the decontamination chamber 400 may be in the range from about 10° C. to about 50° C., and in one embodiment in the range from about 15° C. to about 50° C., and in one embodiment in the range from about 15° C. to about 30° C. The relative humidity of the decontaminant air stream entering the decontamination chamber 400 may be in the range from about 0 to about 50%, and in one embodiment in the range from about 20 to about 40% by volume. The term "relative humidity" is used herein to refer to the ratio of the partial pressure of water vapor in the decontaminant air stream to the saturated vapor pressure of water at the temperature of the decontaminant air stream expressed in terms of percentage. The concentration of decontaminant in the decontaminant air stream entering the decontamination chamber may be in the range from about 0.01 to about 2% by volume, and in one embodiment in the range from about 0.01 to about 1.5% by volume, and in one embodiment in the range from about 0.01 to about 1% by volume, and in one embodiment in the range from about 0.01 to about 0.5% by volume, and in one embodiment in the range from about 0.02 to about 0.2% by volume, and in one embodiment in the range from about 0.02 to about 0.05% by volume. When the decontaminant comprises solvent, the concentration of decontaminant plus solvent in the decontaminant air stream entering the decontamination chamber may be in the range from about 0.01 to about 2% by volume, and in one embodiment in the range from about 0.02 to about 0.08% by volume. When the decontaminant comprises an alkaline gas, the concentration of alkaline gas in the decontaminant air stream entering the decontamination chamber may be in the range from about 0.001 to about 0.01% by volume, and in one embodiment in the range from about 0.003 to about 0.005% by volume. The gas flow rate through the decontamination chamber 400 may be in the range from about 5 to about 40 cubic feet per minute (CFM) (0.14 to 1.13 cubic meters per minute (CMM)), and in one embodiment in the range from about 10 to about 20 CFM (0.28 to 0.57 CMM). The temperature within the decontamination chamber may be in the range from about 10° C. to about 50° C., and in one embodiment in the range from about 15° C. to about 50° C., and in one embodiment in the range from about 15° C. to about 30° C. The operating pressure within the decontamination chamber 400 may be slightly negative to prevent the leakage of contaminants and decontaminants from the decontamination chamber 400. The internal pressure may be in the range of up to about 10 inches of water below atmospheric pressure, and in one embodiment in the range from about 0.01 to about 5 inches of water, and in one embodiment in the range from about 0.01 to about 2 inches of water, and in one embodiment in the range from about 0.01 to about 1 inch of water, and in one embodiment in the range from about 0.01 to about 0.5 inch of water, and in one embodiment in the range from about 0.01 to about 0.3 inch of water below atmospheric pressure.

The contaminated articles may be contaminated with any contaminant. The articles may comprise any article that may be stored in the decontamination chamber 400. These may include military weapons, clothing, and body armor, as well as sensitive equipment such as computers, test equipment, optical devices, electronic devices, communications equipment, and the like. The contaminant may comprise one or more chemical, biological, radiological and/or nuclear (CBRN) warfare agents.

Different levels of decontamination may be accomplished within the decontamination chamber 400. As used herein, the term "decontamination," is intended to encompass both microbial decontamination as well as chemical decontamination—the destruction of chemical agents, or their conversion to harmless or odorless compounds. Decontamination may also encompass the neutralizing of unpleasant odors, such as tobacco smoke, perfume, or body odor residues, and odors and dampness due to molds. "Microbial decontamination" may be used herein to encompass the destruction of biological contaminants, specifically, living microorganisms, and also the destruction or inactivation of pathogenic forms of proteinaceous-infectious agents (prions). The term microbial decontamination encompasses sterilization, the highest level of biological contamination control, which connotes the destruction of all living microorganisms. The term also includes disinfection, the destruction of harmful microorganisms, and sanitizing, which connotes being free from germs. "Chemical decontamination" is intended to encompass the destruction of pathogenic chemical agents or their conversion to less harmful or odiferous species.

Exemplary biological contaminants which may be destroyed in the decontamination process include bacterial spores, vegetative bacteria, viruses, molds, and fungi. Some of these may be capable of killing or causing severe injury to mammals, particularly humans. Included among these are viruses, such as equine encephalomyelitis and smallpox, the coronavirus responsible for Severe Acute Respiratory Syndrome (SARS); bacteria, such as those which cause plague (*Yersina pestis*), anthrax (*Bacillus anthracis*), and tularemia (*Francisella tularensis*); and fungi, such as coccidioidomycosis; as well as toxic products expressed by such microorganisms; for example, the botulism toxin expressed by the common *Clostridium botulinium* bacterium.

Also included are the less harmful microorganisms, such as those responsible for the common cold (rhinoviruses), influenza (orthomyxoviruses), skin abscesses, toxic shock syndrome (*Staphylococcus aureus*), bacterial pneumonia (*Streptococcus pneumoniae*), stomach upsets (*Escherichia coli, Salmonella*), and the like.

Exemplary pathogenic chemical agents may include substances which are often referred to as chemical warfare agents, such as poison gases and liquids, particularly those which are volatile, such as nerve gases, blistering agents (also known as vesicants), and other extremely harmful or toxic chemicals. As used herein, the term "chemical pathogenic agent" is intended to include only those agents which are effective in relatively small dosages to substantially disable or kill mammals and which can be degraded or otherwise rendered harmless by a process which includes oxidation.

Exemplary chemical pathogenic agents may include choking agents, such as phosgene; blood agents, which act on the enzyme cytochrome oxidase, such as cyanogen chloride and hydrogen cyanide; incapacitating agents, such as 3-quinuclidinyl benzilate ("BZ"), which blocks the action of acetylcholine; vesicants, such as di(2-chloroethyl) sulfide (mustard gas or "HD") and dichloro(2-chlorovinyl)arsine (Lewisite); nerve agents, such as ethyl-N,N dimethyl phosphoramino cyanidate (Tabun or agent GA), o-ethyl-S-(2-diisopropyl aminoethyl) methyl phosphono-thiolate (agent VX), isopropyl methyl phosphonofluoridate (Sarin or Agent GB), methylphosphonofluoridic acid 1,2,2-trimethylpropyl ester (Soman or Agent GD).

While the disclosed invention has been explained in relation to various detailed embodiments, it is to be understood that various modifications thereof may become apparent to those skilled in the art upon reading the specification. Therefore, it is to be understood that the invention specified herein is intended to include such modifications as may fall within the scope of the appended claims.

The invention claimed is:

1. A process for operating a self-contained transportable decontamination unit comprising:

a housing containing a decontamination chamber and a decontaminant processing section; and a military master pallet on which the housing is positioned;

the decontamination chamber comprising a first entrance with a first door, the first entrance being adapted for placing articles to be decontaminated in the decontamination chamber, and an opposite second entrance with a second door, the second entrance being adapted for removing decontaminated articles from the decontamination chamber, the decontamination chamber including at least one gas inlet for admitting a decontaminant air stream into the decontamination chamber from the decontaminant processing section and at least one gas outlet for permitting a gaseous air stream to flow out of the decontamination chamber into the decontaminant processing section;

the decontaminant processing section comprising a power generator and a decontaminant generator, the power generator being adapted for providing electrical operating power for the decontaminant generator, the decontaminant generator being adapted for destroying residual amounts of decontaminant in the gaseous air stream, dehumidifying the gaseous air stream, and adding decontaminant to the gaseous air stream to form the decontaminant air stream;

wherein the housing and the decontamination chamber are (1) hardened to ensure that five exposures to chemical, biological, radiological or nuclear contaminants, decontaminants and decontaminating procedures over a thirty-day period do not cause the housing or decontamination chamber to require corrective maintenance during that thirty-day period; (2) constructed to withstand temperatures ranging from about −32° C. to about 49° C.; (3) constructed to withstand relative humidities ranging from about 5% to about 100%; and (4) constructed to operate when exposed to conventional hazards of solar radiation, rain, fungus, salt fog, sand, dust, vibration and shock; and wherein the power generator and decontaminant generator are ruggedized, the process comprising:

opening the first door;

placing one or more contaminated articles in the decontamination chamber;

closing the first door;

operating the power generator to provide power to operate the decontaminant generator;

flowing the decontaminant air stream from the decontaminant processing section into the decontamination chamber;

contacting the contaminated articles in the decontamination chamber with the decontaminant air stream to decontaminate the contaminated articles;

flowing the gaseous air stream from the decontamination chamber back to decontaminant processing section;

opening the second door; and removing the decontaminated articles from the decontamination chamber.

2. The process of claim 1 wherein the decontaminant comprises a peracid, peroxide, hypochlorite, ozone, or a mixture of two or more thereof.

3. The process of claim 2 wherein the decontaminant further comprises a solvent.

4. The process of claim 2 wherein the decontaminant further comprises an alkaline gas.

5. The process of claim 1 wherein the decontaminant comprises hydrogen peroxide.

6. The process of claim 1 wherein the decontaminant comprises vaporous hydrogen peroxide and ammonia.

7. The process of claim 1 wherein the contaminated articles comprise one or more of military weapons, clothing, body armor, computers, test equipment, optical devices, electronic devices and/or communications equipment.

8. The process of claim 1 wherein the contaminated articles are contaminated with one or more chemical, biological, radiological and/or nuclear warfare agents.

9. The process of claim 1 wherein the contaminated articles are contaminated with one or more bacterial spores, vegetative bacteria, viruses, molds and/or fungi.

10. The process of claim 1 wherein the contaminated articles are contaminated with one or more pathogenic chemical agents.

11. The process of claim 1 wherein the step of contacting the contaminated articles with the decontaminant air stream comprises a dry process characterized by the absence of condensate formation on the surface of the contaminated articles being decontaminated.

12. The process of claim 1 wherein the step of contacting the contaminated articles with the decontaminant air stream comprises a wet process characterized by the formation of condensate on the surface of the contaminated articles being decontaminated.

13. The process of claim 12 wherein the condensate comprises hydrogen peroxide.

* * * * *